(12) United States Patent
Uehara et al.

(10) Patent No.: US 11,986,303 B2
(45) Date of Patent: May 21, 2024

(54) BIOLOGICAL INFORMATION MEASUREMENT DEVICE, BIOLOGICAL INFORMATION MEASUREMENT METHOD, AND MEDIUM STORING BIOLOGICAL INFORMATION MEASUREMENT PROGRAM

(71) Applicant: Fukuoka University, Fukuoka (JP)

(72) Inventors: Yoshinari Uehara, Fukuoka (JP);
Takuro Matsuda, Fukuoka (JP);
Yukiya Tanoue, Fukuoka (JP)

(73) Assignee: Fukuoka University, Fukuoka (JP)

( * ) Notice: Subject to any disclaimer, the term of this patent is extended or adjusted under 35 U.S.C. 154(b) by 382 days.

(21) Appl. No.: 17/603,751

(22) PCT Filed: Apr. 16, 2020

(86) PCT No.: PCT/JP2020/016762
§ 371 (c)(1),
(2) Date: Oct. 14, 2021

(87) PCT Pub. No.: WO2020/213689
PCT Pub. Date: Oct. 22, 2020

(65) Prior Publication Data
US 2022/0175288 A1    Jun. 9, 2022

(30) Foreign Application Priority Data

Apr. 17, 2019 (JP) ................................ 2019-078637

(51) Int. Cl.
*A61B 5/22* (2006.01)

(52) U.S. Cl.
CPC .................................. *A61B 5/222* (2013.01)

(58) Field of Classification Search
CPC ...................................................... A61B 5/222
See application file for complete search history.

(56) References Cited

U.S. PATENT DOCUMENTS 8,412,315 B2 * 4/2013 Ross ................... A61B 5/02405
600/515
2005/0154326 A1 * 7/2005 Martynenko ............ A61B 5/00
600/515

(Continued)

FOREIGN PATENT DOCUMENTS

JP      2007-181486 A     7/2007
JP      2012239666 A     12/2012

(Continued)

OTHER PUBLICATIONS

English International Search Report of PCT/JP2020/016762 mailed Jun. 30, 2020.

(Continued)

*Primary Examiner* — Catherine M Voorhees
(74) *Attorney, Agent, or Firm* — Muncy, Geissler, Olds & Lowe, P.C.

(57) ABSTRACT

A biological information measurement device includes a heart rate counting unit for measuring an HR value indicating a heart rate on a basis of heart-rate data obtained by capturing heartbeats when a subject to be measured exercises, an analysis unit for performing power spectrum analysis on a heart rate variability frequency of the heart-rate data to calculate an LF value which is an integral value of low frequency components, and a detection unit for obtaining an HR/LF value by dividing the HR value by the LF value with respect to exercise intensity of the subject to be measured.

6 Claims, 6 Drawing Sheets

(56) References Cited

U.S. PATENT DOCUMENTS

| | | | |
|---|---|---|---|
| 2009/0082681 A1* | 3/2009 | Yokoyama | A61B 5/024 |
| | | | 600/595 |
| 2013/0231576 A1 | 9/2013 | Tanaka | |
| 2016/0292271 A1* | 10/2016 | Kim | G10H 1/40 |
| 2019/0110759 A1* | 4/2019 | Tanishima | A61B 5/4035 |
| 2021/0000355 A1* | 1/2021 | Zukawa | A61B 5/01 |

FOREIGN PATENT DOCUMENTS

| | | |
|---|---|---|
| JP | 2016214491 A | 12/2016 |
| WO | 2012050088 A1 | 4/2012 |

OTHER PUBLICATIONS

International Preliminary Report on Patentability of PCT/JP2020/016762 issued Sep. 28, 2021, which includes Written Opinion of the International Searching Authority for PCT/JP2020/016762 and English translation thereof.

* cited by examiner

LACTATE THRESHOLD (LT) = EXERCISE INTENSITY OF 100%

VENTILATION THRESHOLD (VT) = EXERCISE INTENSITY OF 100%

(A) LACTATE THRESHOLD (LT) = EXERCISE INTENSITY OF 100%

(B) VENTILATION THRESHOLD (VT) = EXERCISE INTENSITY OF 100%

BIOLOGICAL INFORMATION MEASUREMENT DEVICE, BIOLOGICAL INFORMATION MEASUREMENT METHOD, AND MEDIUM STORING BIOLOGICAL INFORMATION MEASUREMENT PROGRAM

TECHNICAL FIELD

The present invention relates to a biological information measurement device, a biological information measurement method, and a biological information measurement program which is capable of measuring exercise intensity of a subject to be measured in real time during exercise.

BACKGROUND ART

Exercise is performed with the aim of promoting health, preventing and treating lifestyle diseases, and training. It is difficult to obtain effects from exercise which places stress on the body if the stress (intensity) is insufficient. It is rather concerned that excessive stress might negatively affect the body. Measurement of a lactate threshold (LT) and a ventilation threshold (VT) is recommended to determine safe and effective exercise intensity. However, skilled engineers and expensive equipment are required to measure these thresholds, which makes it difficult to popularize the measurement.

For example, an exercise stress measurement device is known as disclosed in Patent Literature 1, which enables each subject to perform exercise with an optimal amount of exercise in accordance with physical strength, or the like, of the subject.

The exercise stress measurement device disclosed in Patent Literature 1 detects fluctuation of a heartbeat interval of a subject who is exercising to detect exercise stress of the subject.

This measurement device detects an integral value (HF power) in a high frequency band and an integral value (LF power) in a low frequency band from a power spectrum obtained by performing Fourier transform on fluctuation of the heartbeat interval of the subject who is exercising and detects exercise stress of the subject from the HF power.

Further, the measurement device detects exercise intensity from a ratio of the HE power (HF value) and the LF power (LF value), converts the HF value, and the ratio of the LF value and the HF value into exercise indexes indicating exercise stress, adds the exercise index converted from the HF value and the exercise index converted with the ratio of the LF value and the HF value and detects exercise stress from the added exercise index.

CITATION LIST

Patent Literature

Patent Literature 1: Japanese Patent Laid-Open No. 2007-181486

SUMMARY OF INVENTION

Technical Problem

The exercise stress measurement device disclosed in Patent Literature 1 detects exercise stress from the HF value which reflects parasympathetic nerve activity and detects exercise stress from the ratio of the LF value and the HF value (LF/HF value) which reflects sympathetic nerve activity. However, the HF value and the LF/HF value do not precipitously increase or decrease with respect to the exercise stress. Thus, the HF value and the LF/HF value are not appropriate as indexes which indicate change of a physical condition or management of a health condition in accordance with exercise intensity.

As illustrated in FIG. 7, if exercise intensity rises, sympathetic nerves become active, and a heart rate rises. The heart rate moderately rises even if the exercise intensity exceeds optimal exercise intensity. It is assumed that this is because a baroceptor which senses change in a blood pressure as rise in the heart rate controls sympathetic nerves to prevent sudden rise of the heart rate. Thus, the heart rate from which influence of the baroceptor is excluded is predicted to precipitously rise if the exercise intensity exceeds the optimal exercise intensity.

Thus, if a new index indicating sympathetic nerve activity can be introduced, it is possible to manage change of a physical condition and a health condition by grasping a state of the sympathetic nerve activity from heart-rate data obtained by capturing heartbeats when the subject moves his/her body also in his/her daily life as well as when the subject exercises hard.

The present invention is therefore directed to providing a biological information measurement device, a biological information measurement method, and a biological information measurement program capable of obtaining biological information which is important for health management by introducing a new index indicating sympathetic nerve activity.

Solution to Problem

The present inventors have found that a value obtained by performing power spectrum analysis on a heart rate variability frequency and dividing the result by an integral value (LF value) of low frequency components as a correction value for a heart rate (HR value) of a subject to be measured becomes a new index which indicates sympathetic nerve activity and have achieved the invention.

In other words, a biological information measurement device of the present invention includes heart rate counting means for measuring an HR value indicating a heart rate on the basis of heart-rate data obtained by capturing heartbeats when a subject to be measured exercises, analysis means for performing power spectrum analysis on a heart rate variability frequency of the heart-rate data to calculate an LF value which is an integral value of low frequency components, and detection means for obtaining an HR/LF value by dividing the HR value by the LF value with respect to exercise intensity of the subject to be measured.

A biological information measurement method of the present invention includes a step of measuring an HR value indicating a heart rate on the basis of heart-rate data obtained by capturing, by heart rate counting means, a condition of heartbeats when a subject to be measured exercises, a step of performing power spectrum analysis on a heart rate variability frequency of the heart-rate data by analysis means to calculate an LF value which is an integral value of low frequency components, and a step of performing detection by detection means for obtaining an HR/LF value by dividing the HR value by the LF value with respect to exercise intensity of the subject to be measured.

A biological information measurement program of the present invention causes a computer to function as heart rate counting means for measuring an HR value indicating a heart rate on the basis of heart-rate data obtained by capturing heartbeats when a subject to be measured exercises, analysis means for performing power spectrum analysis on a heart rate variability frequency of the heart-rate data to calculate an LF value which is an integral value of low frequency components, and detection means for obtaining an HR/LF value by dividing the HR value by the LF value with respect to exercise intensity of the subject to be measured.

According to the present invention, the heart rate counting means measures an HR value indicating a heart rate, the analysis means calculates an HF value which is an integral value of high frequency components of the heart rate variability frequency, and an LF value which is an integral value of low frequency components, and the detection means obtains an HR/LF value by dividing the HR value by the LF value with respect to exercise intensity of the subject to be measured. As a result, it is possible to obtain biological information which is important for health management by recognizing tendency of the HR/LF value with respect to the exercise intensity.

The detection means can detect a point at which the HR/LF value obtained with respect to the exercise intensity precipitously increases with a reference set in advance. As a result of this, it is possible to estimate this point as optimal exercise intensity.

The present inventors have found that an HF value and an HR/LF value in different units can be dealt with as dimensionless quantity by setting both the HF value and the HR/LF value at logarithms having 10 as a base.

Thus, the present inventors have found that in a graph which indicates exercise intensity on a horizontal axis and indicates a logarithmic value on a vertical axis, an intersection of linear approximations of the HF value and the HR/LF value is obtained, and the intersection matches or becomes a value close to optimal exercise intensity.

Thus, the analysis means can calculate an HF value which is an integral value of high frequency components through power spectrum analysis, and the detection means can detect a first intersection of a first approximation line obtained by linearly approximating a logarithm of the HF value with respect to exercise intensity of the subject to be measured and a second approximation line obtained by linearly approximating a logarithm of the obtained HR/LF value.

The logarithm of the HR/LF value linearly rises during incremental exercise stress, and thus, the first intersection of the first approximation line and the second approximation line can be clearly obtained, so that the first intersection can be obtained as optimal exercise intensity.

The detection means can detect a second intersection of the first approximation line and a third approximation line obtained by linearly approximating a logarithm of an LF/HF value obtained by dividing the LF value by the HF value and can detect a range of exercise intensity indicated by the first intersection and the second intersection.

As a result of a range being provided by the second intersection to the optimal exercise intensity indicated by the first intersection, even in a case where the first intersection slightly deviates from the optimal exercise intensity, by a range being provided to the optimal exercise intensity, the optimal exercise intensity which varies between individuals can be included in the range. It is therefore possible to further improve accuracy of detection of the optimal exercise intensity.

Advantageous Effects of Invention

According to the present invention, an HR/LF value linearly rises during incremental exercise stress, which enables a first intersection of a first approximation line and a second approximation line to be clearly obtained, and thus, the first intersection can be obtained as optimal exercise intensity, so that it is possible to improve accuracy of detection of optimal exercise intensity.

DESCRIPTION OF EMBODIMENT

Embodiment

A biological information measurement device according to an embodiment of the present invention will be described on the basis of the drawings.

Figure 1:
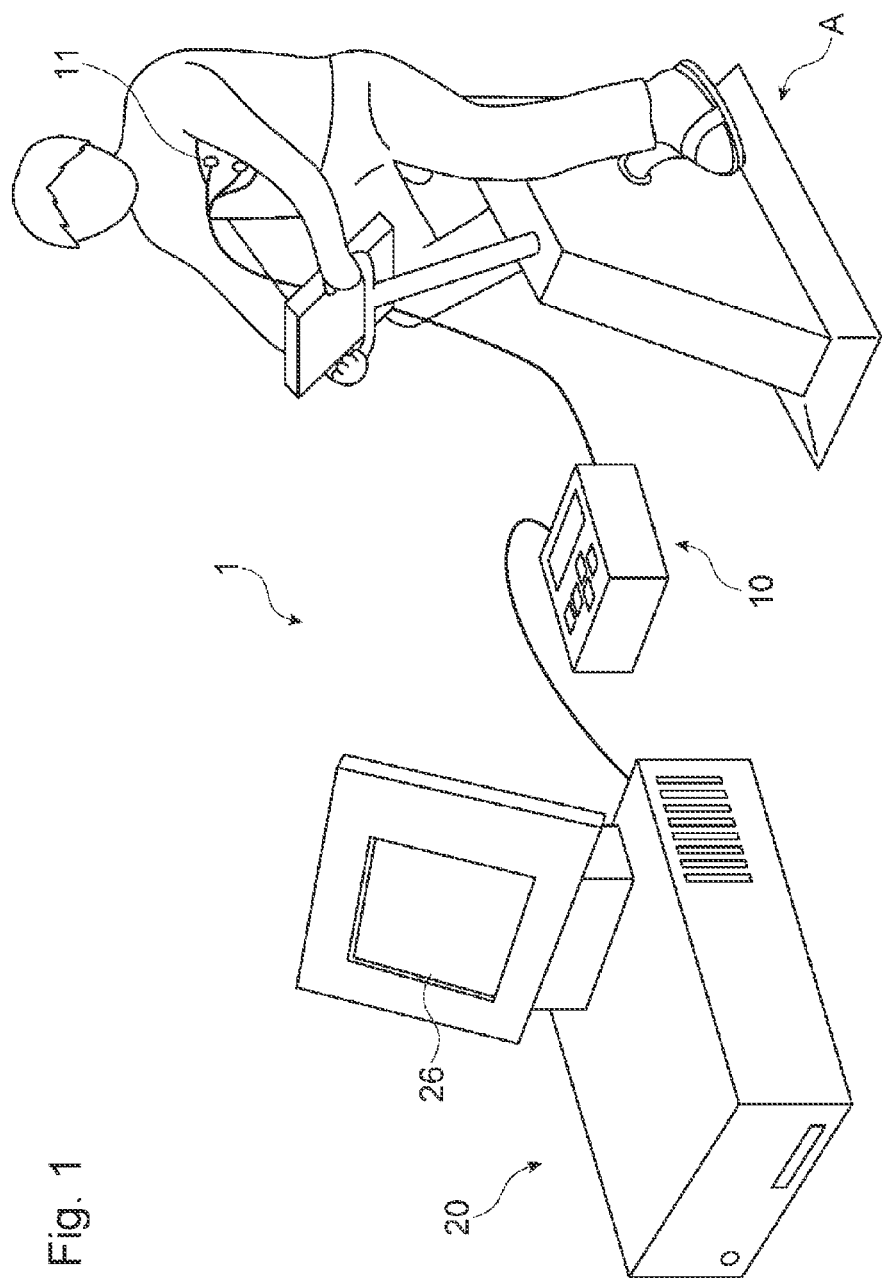
FIG. 1 is a view illustrating a subject to be measured for whom exercise stress is measured by a biological information measurement device according to an embodiment of the present invention.

As illustrated in FIG. 1, a biological information measurement device 1 measures a state where a subject to be measured performs exercise with stress using equipment A which places exercise stress and measures biological information which is important for health management. For example, a bicycle ergometer can be used as the equipment A which places exercise stress. Further, a treadmill may be used as the equipment which places exercise stress. Still further, the subject to be measured may actually run on a road or go up and down a step as exercise stress.

Figure 2:
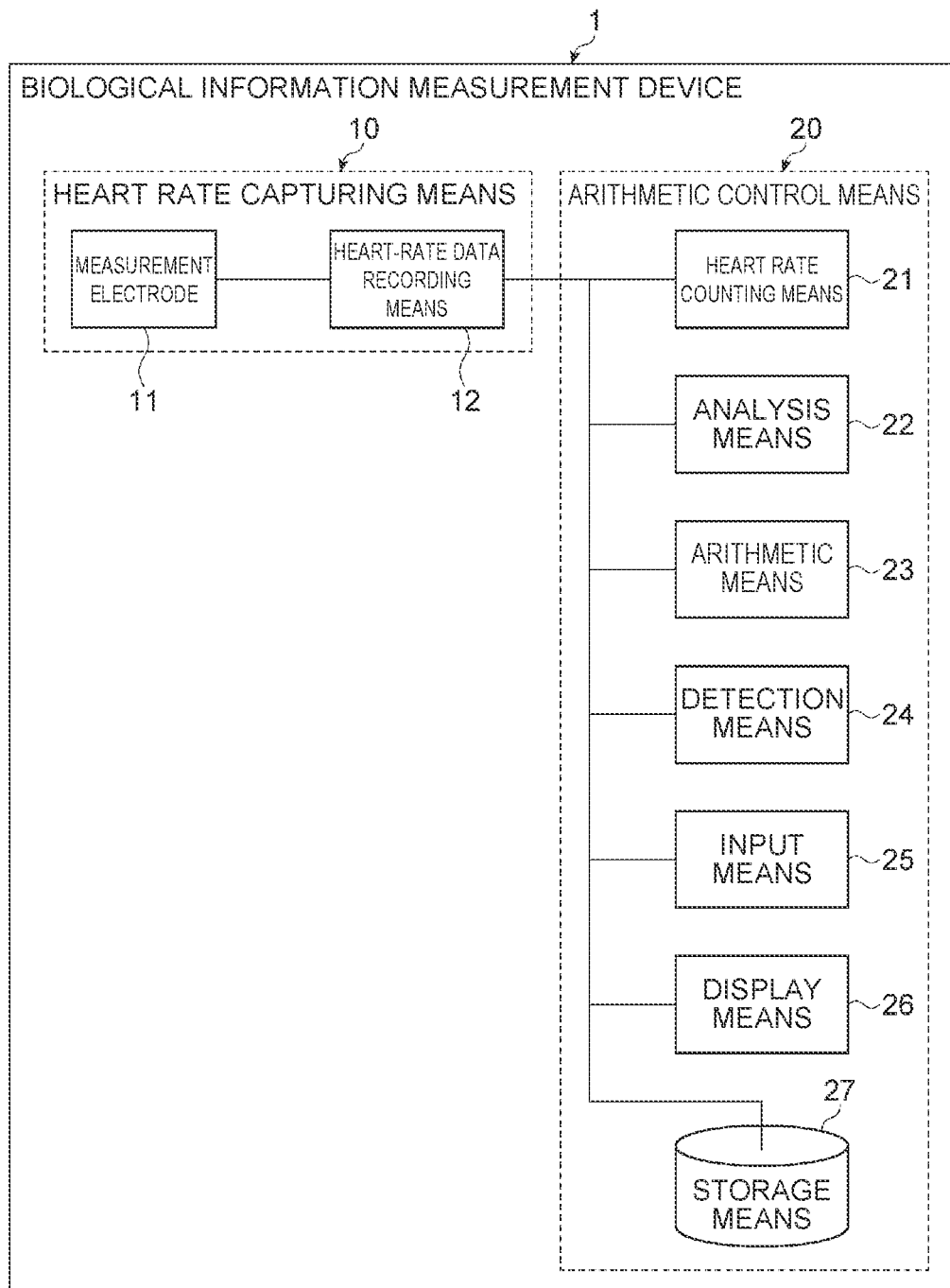
FIG. 2 is a view for explaining a configuration of the biological information measurement device illustrated in FIG. 1.

As illustrated in FIG. 2, the biological information measurement device 1 includes heart rate capturing means 10 and arithmetic control means 20.

The heart rate capturing means 10 captures heartbeats from the subject to be measured and outputs the heartbeats as heart-rate data. For example, LRR-03 or HRR-01 manufactured by Arm Electronics Co., Ltd. can be used as the heart rate capturing means 10. The heart rate capturing means 10 includes a measurement electrode 11 and heart-rate data recording means 12.

The measurement electrode 11 is an electrocardiogram electrode which is to be attached to the subject to be measured.

The heart-rate data recording means 12 converts an analog signal from the measurement electrode 11 into a digital signal and outputs the digital signal to the arithmetic control means 20 while storing the digital signal in storage means.

The arithmetic control means 20 is a computer which detects optimal exercise intensity of the subject to be measured on the basis of the heart-rate data. This computer functions as the arithmetic control means 20 of the biological information measurement device 1 by running a biological information measurement program.

The arithmetic control means 20 includes heart rate counting means 21, analysis means 22, arithmetic means 23, detection means 24, input means 25, display means 26 and storage means 27.

The heart rate counting means 21 measures an HR value which indicates a heart rate on the basis of the heart-rate data.

The analysis means 22 performs power spectrum analysis on a heart rate variability frequency of the heart-rate data and outputs an HF value which is an integral value of high frequency components and an LF value which is an integral value of low frequency components.

The arithmetic means 23 calculates an HR/LF value by dividing an HR value by the LF value as correction of the HR value. Further, the arithmetic means 23 calculates an LF/HF value by dividing the LF value by the HF value.

The detection means 24 detects a point at which the HR/LF value obtained with respect to exercise intensity precipitously rises. The point at which the HR/LF value precipitously rises can be detected from an HR/LF value when the HR/LF value is greater with a reference set in advance. In this event, whether or not the HR/LF value exceeds a reference value may be determined by simply comparing the HR/LF value and the reference value, or whether or not a differential of the HR/LF value with respect to exercise intensity exceeds a reference value may be determined.

Further, the detection means 24 detects a first intersection of a first approximation line obtained by linearly approximating a logarithm of the HF value with respect to exercise intensity of the subject to be measured and a second approximation line obtained by linearly approximating a logarithm of the HR/LF value. Further, the detection means 24 detects a second intersection of the first approximation line and a third approximation line obtained by linearly approximating the LF/HF value.

The input means 25 starts or stops the biological information measurement program or gives an instruction to cause a result to be displayed at the display means 26. The input means 25 can be implemented as a keyboard or a mouse. Further, the display means 26 can be implemented as a CRT, an LCD or an organic EL display.

The storage means 27 is a non-volatile memory to and from which respective pieces of data can be written and read. A large capacity, fast access hard disk device can be employed as the storage means 27.

In addition to the heart-rate data, the HR value, the HF value, the LF value, the HR/LF value and the LF/HF value, an OS, the biological information measurement program, setting information, and the like, are stored in this storage means 27.

An operating state and a measurement method of the biological information measurement device 1 according to the embodiment of the present invention configured as described above will be described on the basis of the drawings.

The heart-rate data which is input from the measurement electrode 11 attached to the subject to be measured and which is acquired by the heart-rate data recording means 12 is output from the heart rate capturing means 10 to the arithmetic control means 20.

At the arithmetic control means 20, first, the heart rate counting means 21 measures an HR value indicating a heart rate on the basis of the heart-rate data captured from the subject to be measured.

Then, the analysis means 22 calculates a power spectrum of a heart rate variability frequency from the heart-rate data. This power spectrum can be obtained by performing operation on the heart-rate data on the basis of a maximum entropy method. Further, the power spectrum can be obtained by performing fast Fourier transform on the heart-rate data.

Then, the analysis means 22 integrates respective power spectrums in a low frequency band (equal to or higher than 0.004 Hz and less than 0.15 Hz) and in a high frequency band (equal to or higher than 0.15 Hz and equal to or less than 0.4 Hz). The analysis means 22 then calculates an integral value of low frequency components as an LF value and an integral value of high frequency components as an HF value.

Then, the arithmetic means 23 calculates an HR/LF value, a logarithm of the HR/LF value, an LF/HF value and a logarithm of the LF/HF value.

The detection means 24 then detects an HR/LF value when the HR/LF value with respect to exercise intensity is greater than a predetermined value (reference set in advance).

In a case where the detection means 24 detects that the HR/LF value is greater than the predetermined value, a graph or a table indicating exercise intensity and the HR/LF value with respect to the exercise intensity is displayed at the display means 26 as a measurement result or printed by a printing device which is not illustrated and output.

Further, the detection means 24 obtains an approximation line (first approximation line) of a logarithm of the HF value with respect to exercise intensity of the subject to be measured. Further, the detection means 24 obtains an approximation line (second approximation line) of the HR/LF value. Then, by the detection means 24 detecting a first intersection of the first approximation line and the second approximation line, a measurement result indicating this first intersection as optimal exercise intensity is displayed at the display means 26 or printed by a printing device which is not illustrated and output.

Figure 3:
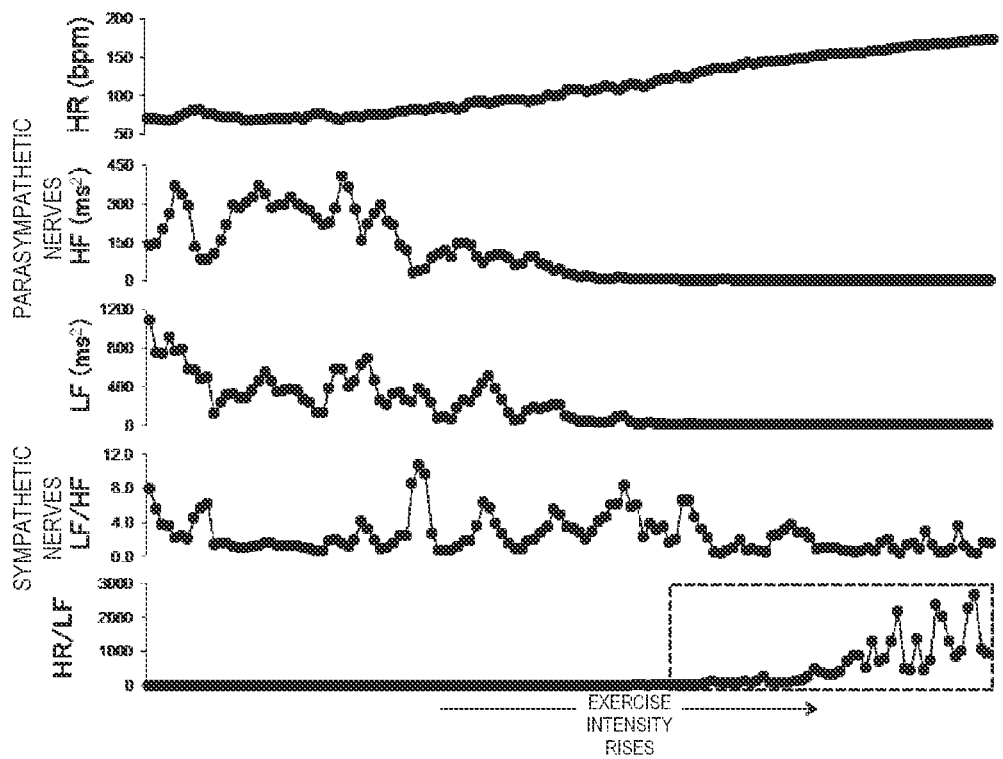
FIG. 3 is a view for explaining tendency of an HR value, an HF value, an LF value, an LF/HF value and an HR/LF value with respect to exercise intensity.

As illustrated in FIG. 3, while the heart rate (HR value) rises in accordance with increase in exercise intensity, if an approximation line is obtained by calculating a logarithm of the heart rate to obtain an intersection with the first approximation line by the HF value indicating parasympathetic nerve activity, this approximation line becomes a substantially horizontal approximation line with no change.

Further, it is obvious that the LF/HF value which is a typical index of sympathetic nerve activity does not show sufficient activity or rapid increase in activity and widely varies.

Thus, the present inventors have found use of the HR/LF value as a new index of sympathetic nerves obtained by correcting this heart rate (HR value) with an LF value which is an index of activity of the whole autonomic nerves (sympathetic nerves+parasympathetic nerves).

EXAMPLE

Here, an example in a case where exercise intensity was measured by the biological information measurement device 1 using eight female college students as subjects to be measured will be described.

A measurer attached the measurement electrodes 11 for measuring heartbeats at three points of an anterior chest and an abdominal area of a female college student who is a subject to be measured and who rides on a bicycle ergometer which is equipment A of placing exercise stress and performed measurement through a Ramp incremental exercise stress test as exercise with stress.

Further, the measurer took a blood sample from the subject to be measured during exercise with stress to measure a blood lactate level and collected an expiratory gas using a mass spectroscope to calculate oxygen intake and carbon dioxide excretion to measure exercise intensity. The expiratory gas was analyzed using ARCO-2000 manufactured by ARCO SYSTEM Inc.

An amount of exercise stress is 82.7±18.5 W in a lactate threshold when a blood lactate level is measured and is 83.8±5.8 W in a ventilation threshold when oxygen intake and carbon dioxide excretion are measured.

Figure 4:
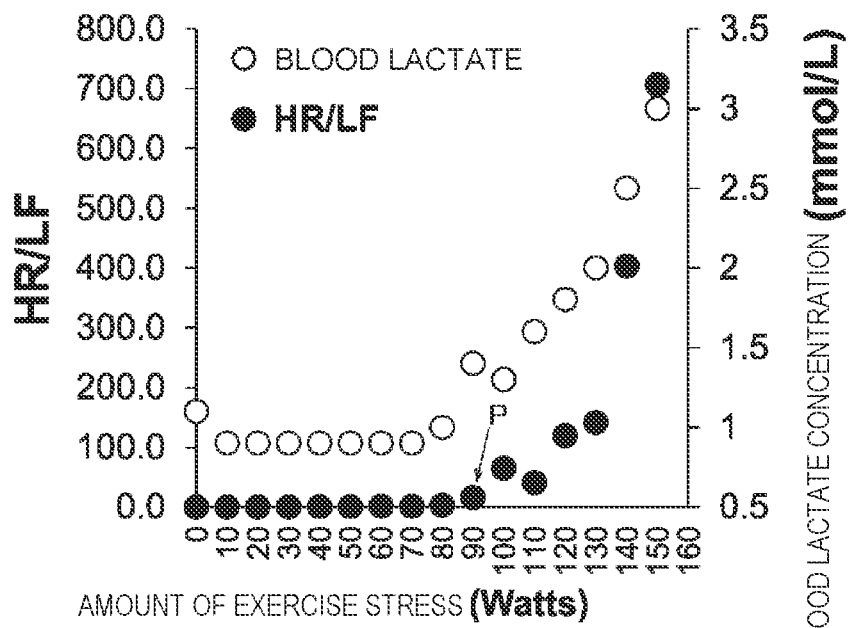
FIG. 4 is a graph which indicates exercise intensity on a horizontal axis and indicates a blood lactate level and an HR/LF value on a vertical axis.

The measurement result is indicated with a graph in FIG. 4.

FIG. 4 is a graph which indicates exercise intensity on a horizontal axis and indicates an HR/LF value and a blood lactate level on a vertical axis. Each point indicates a numerical value of one subject.

It is clear from FIG. 4 that the HR/LF value precipitously rises from 90 W indicated with a point P.

The HR/LF value was 16.1 at 90 W. The HR/LF value at 70 W before the HR/LF value reached 90 W was 1.6 and was 3.0 at 80 W. Further, the HR/LF value was 64.8 at 100 W and was 40.5 at 110 W.

The subject can grasp this point P as exercise intensity when sympathetic nerves start to actively operate. Further, exercise intensity at the point P can be estimated as optimal exercise intensity.

Thus, by the subject to be measured recognizing tendency of the HR/LF value with respect to exercise intensity as indicated in the graph in FIG. 4, the subject to be measured can make use of the tendency when he/she makes a plan for exercise or can grasp influence of activity in daily life on the body.

In this manner, by introducing the HR/LF value as a new index indicating sympathetic nerve activity, it is possible to obtain biological information which is important for health management.

Figure 5A:
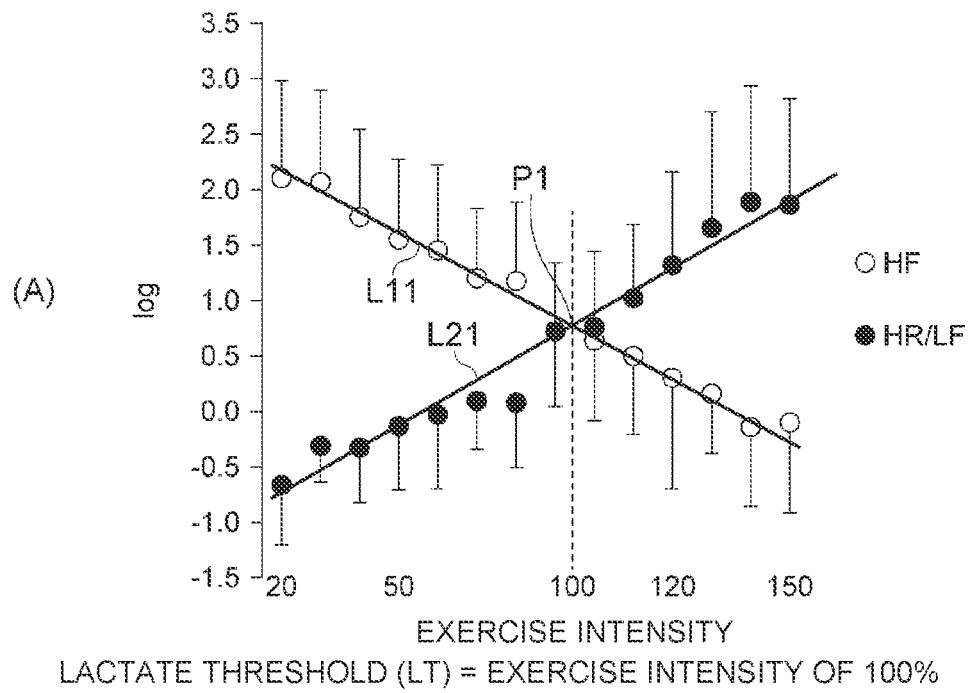
FIG. 5 is a graph which indicates exercise intensity on a horizontal axis and indicates a logarithm of the HF value and a logarithm of the HR/LF value on a vertical axis, in which FIG. 5(A) indicates a case where exercise stress when the blood lactate level is measured and a lactate threshold (LT) is detected is set at 100%, and FIG. 5(B) indicates a case where exercise stress when oxygen intake and carbon dioxide excretion are measured from an expiratory gas and a ventilation threshold (VT) is detected is set at 100% (optimal exercise intensity).
Figure 5B:
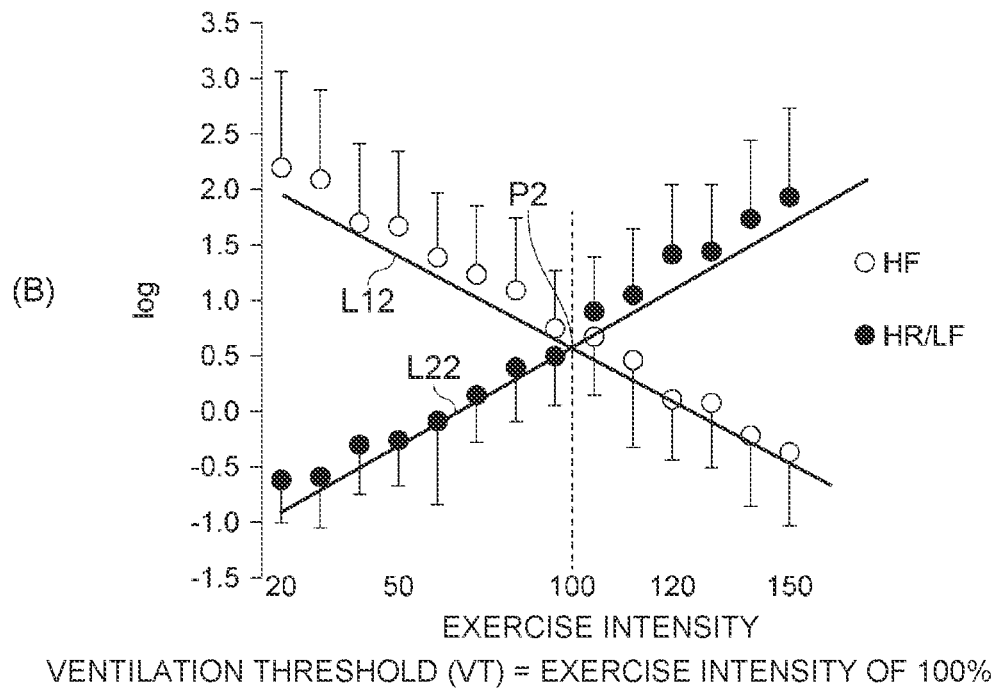

FIG. 5(A) and FIG. 5(B) indicate exercise intensity on a horizontal axis and indicate a logarithm of the HF value and a logarithm of the HR/LF value on a vertical axis. Each point indicates an average value, and standard deviation is indicated with an error bar.

In the graph indicated in FIG. 5(A), exercise stress when a blood lactate level is measured and a lactate threshold (LT) is detected is set at 100% (optimal exercise intensity) for exercise intensity.

From the graph in FIG. 5(A), a first approximation line L11 by the logarithm of the HF value can be expressed with the following expression 1.

$Y=-0.018X+2.503$ (correlation coefficient $R=0.995$)  (Expression 1)

Further, from the graph in FIG. 5(A), a second approximation line L21 by the HR/LF value can be expressed with the following expression 2.

$Y=0.020X-1.174$ (correlation coefficient $R=0.982$)  (Expression 2)

Thus, a first intersection P1 of the first approximation line L11 by expression 1 and the second approximation line L21 by expression 2 is located at exercise stress of 100% by the LT, so that it can be understood that this first intersection P1 substantially indicates optimal exercise intensity.

In the graph indicated in FIG. 5(B), exercise stress when oxygen intake and carbon dioxide excretion are measured from an expiratory gas and a ventilation threshold (VT) is detected is set at 100% (optimal exercise intensity) for exercise intensity.

From the graph in FIG. 5(B), a first approximation line L12 by the HF value can be expressed with the following expression 3.

$Y=-0.020X+2.620$ (correlation coefficient $R=0.997$)  (Expression 3)

Further, from the graph in FIG. 5(B), a second approximation line L22 by the HR/LF value can be expressed with the following expression 4.

$Y=0.021X-1.224$ (correlation coefficient $R=0.994$)  (Expression 4)

Thus, a first intersection P2 of the first approximation line L12 by expression 3 and the second approximation line L22 by expression 4 is located at exercise stress of 100% by the VT, so that it can be understood that this first intersection P2 substantially indicates optimal exercise intensity.

In this manner, it is obvious from FIG. 5(A) and FIG. 5(B) that the logarithm of the HR/LF value (second approximation lines L21 and L22) linearly rises during incremental exercise stress, so that the first intersections P1 and P2 can be clearly obtained between the logarithm of the HR/LF value (second approximation lines L21 and L22) and the logarithm of the HF value (first approximation lines L11 and L12).

Thus, by the detection means 24 obtaining the first intersections P1 and P2 from expression 1 and expression 3 indicating the first approximation lines L11 and L12 and expression 2 and expression 4 indicating the second approximation lines L21 and L22, it is possible to accurately obtain optimal exercise intensity without measuring the LT and the VT.

It is therefore not necessary to take a blood sample from the subject to be measured during exercise with stress and it is not necessary for the subject to be measured to wear a mask for collecting an expiratory gas, so that non-invasive measurement can be achieved.

Figure 6A:
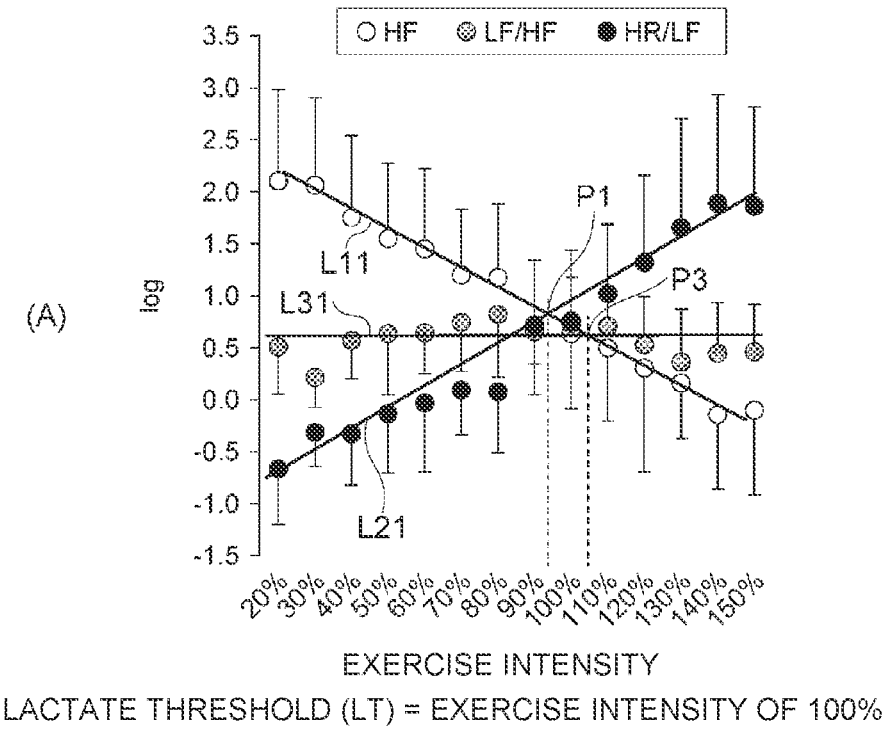
FIG. 6(A) and FIG. 6(B) are a graph in which an approximation line (third approximation line) by a logarithm of the LF/HF value is superimposed on the graph indicated in FIG. 5.
Figure 6B:
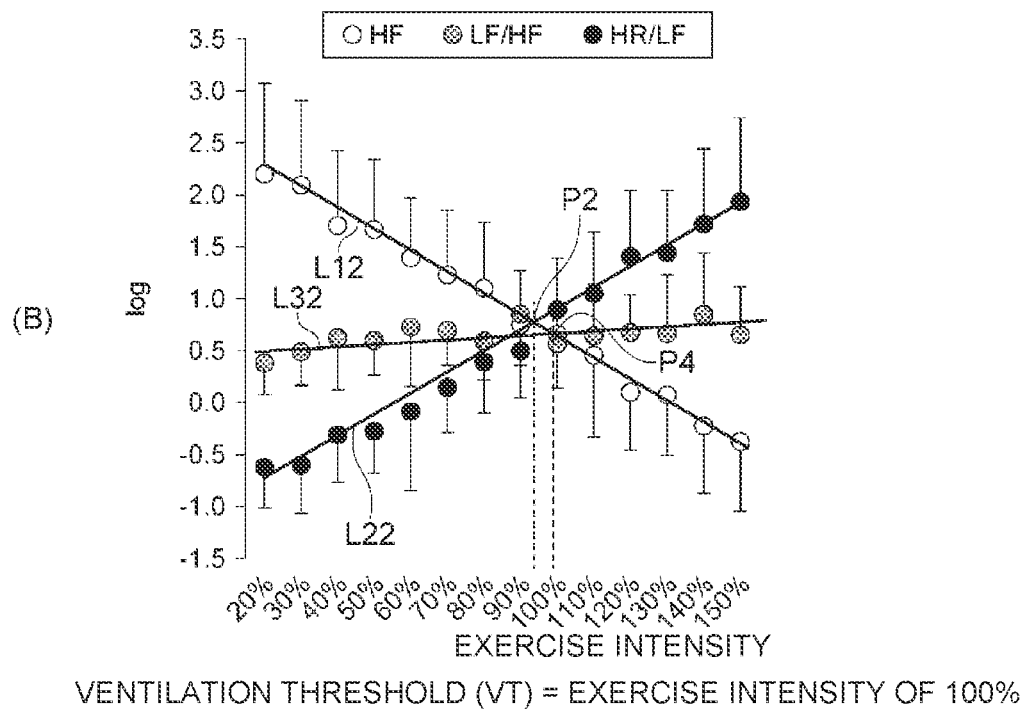
Figure 7:
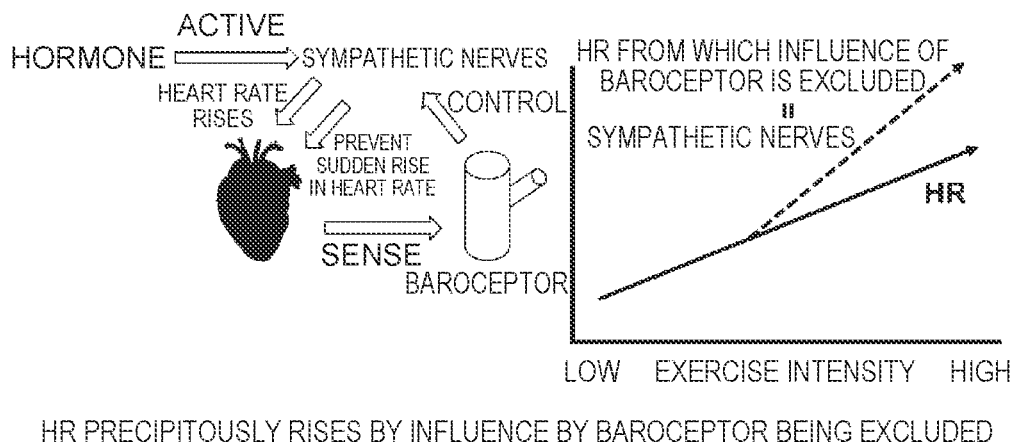
FIG. 7 is a view for explaining relationship between a heart rate and sympathetic nerves.

The detection means 24 can obtain second intersections P3 and P4 of the first approximation lines L11 and L12 and third approximation lines L31 and L32 as indicated in FIG. 6(A) and FIG. 6(B) by superimposing approximation lines (third approximation lines) by the logarithm of the LF/HF value which reflects sympathetic nerve activity on the graphs indicated in FIG. 5(A) and FIG. 5(B).

Note that from the graph indicated in FIG. 6(A), the third approximation line L31 can be expressed with the following expression 5.

$Y=-0.0001X+0.584 (R=0.034)$  (Expression 5)

Further, from the graph indicated in FIG. 6(B), the third approximation line L32 can be expressed with the following expression 6.

$Y=0.002X+0.496 (R=0.580)$  (Expression 6)

FIG. 6(A) is a graph in which the third approximation line L31 is superimposed on the graph in FIG. 5(A). As can be seen from FIG. 6(A), when the lactate threshold (LT) is set at exercise intensity of 100%, the second intersection P3 of the first approximation line L11 and the third approximation line L31 indicates exercise intensity of approximately 110%.

Further, as can be seen from FIG. 6(B), when the ventilation threshold (VT) is set at exercise intensity of 100%, the second intersection P4 of the first approximation line L12 and the third approximation line L32 indicates exercise intensity of approximately 105%.

From this, the optimal exercise intensity can be set in a range of exercise intensity indicated by the first intersections P1 and P2 of the first approximation lines L11 and L12 and the second approximation lines L21 and L22 and the second intersections P3 and P4 of the first approximation lines L11 and L12 and the third approximation lines L31 and L32.

Further, by the detection means 24 displaying this range of exercise intensity at the display means 26 or printing the range by a printing device which is not illustrated and outputting the range, the subject to be measured can recognize that the optimal exercise intensity is included within the range.

Thus, by a range being provided by the second intersections P3 and P4 to the optimal exercise intensity indicated by the first intersections P1 and P2, even if the first intersection slightly deviates from the optimal exercise intensity, the optimal exercise intensity which varies between individuals can be included in the range. It is therefore possible to further improve accuracy of detection of optimal exercise intensity.

INDUSTRIAL APPLICABILITY

According to the present invention, optimal exercise intensity can be detected with high accuracy, and thus, the present invention is suitable for promoting health, preventing and treating lifestyle diseases, and training.

REFERENCE SIGNS LIST 1 biological information measurement device
10 heart rate capturing means
11 measurement electrode
12 heart-rate data recording means
20 arithmetic control means
21 heart rate counting means
22 analysis means
23 arithmetic means
24 detection means
25 input means
26 display means
27 storage means
A equipment which places exercise stress
L11, L12 first approximation line
L21, L22 second approximation line
L31, L32 third approximation line
P1, P2, P3, P4 intersection

The invention claimed is:

1. A biological information measurement device comprising:
heart rate counting means for measuring an HR value indicating a heart rate on a basis of heart-rate data obtained by capturing heartbeats when a subject to be measured exercises;
analysis means for performing power spectrum analysis on a heart rate variability frequency of the heart-rate data to calculate an LF value which is an integral value of low frequency components; and
detection means for obtaining an HR/LF value by dividing the HR value by the LF value with respect to exercise intensity of the subject to be measured.

2. The biological information measurement device according to claim 1,
wherein the detection means detects a point at which the HR/LF value obtained with respect to exercise intensity precipitously increases with a reference set in advance.

3. The biological information measurement device according to claim 1,
wherein the analysis means calculates an HF value which is an integral value of high frequency components through power spectrum analysis, and
the detection means detects a first intersection of a first approximation line obtained by linearly approximating a logarithm of the HF value with respect to exercise intensity of the subject to be measured and a second approximation line obtained by linearly approximating a logarithm of the obtained HR/LF value.

4. The biological information measurement device according to claim 3,
wherein the detection means detects a second intersection of the first approximation line and a third approximation line obtained by linearly approximating a logarithm of an LF/HF value obtained by dividing the LF value by the HF value and detects a range of exercise intensity indicated by the first intersection and the second intersection.

5. A biological information measurement method comprising:
a step of measuring an HR value indicating a heart rate on a basis of heart-rate data obtained by capturing, by heart rate counting means, a condition of heartbeats when a subject to be measured exercises;
a step of performing power spectrum analysis on a heart rate variability frequency of the heart-rate data by analysis means to calculate an LF value which is an integral value of low frequency components; and
a step of performing detection by detection means for obtaining an HR/LF value by dividing the HR value by the LF value with respect to exercise intensity of the subject to be measured.

6. A non-transitory storage medium storing a biological information measurement program for causing a computer to function as:
heart rate counting means for measuring an HR value indicating a heart rate on a basis of heart-rate data obtained by capturing heartbeats when a subject to be measured exercises;
analysis means for performing power spectrum analysis on a heart rate variability frequency of the heart-rate data to calculate an LF value which is an integral value of low frequency components; and
detection means for obtaining an HR/LF value by dividing the HR value by the LF value with respect to exercise intensity of the subject to be measured.

* * * * *